(12) United States Patent
Chen et al.

(10) Patent No.: US 9,343,275 B1
(45) Date of Patent: May 17, 2016

(54) METHODS FOR CHARACTERIZING CARBON OVERCOAT

(75) Inventors: Lifan Chen, Fremont, CA (US);
Haifeng Wang, Morgan Hill, CA (US);
Liang Hong, Pleasanton, CA (US);
Nattaporn Khamnualthong, Lamlukka (TH)

(73) Assignee: Western Digital (Fremont), LLC, Fremont, CA (US)

(*) Notice: Subject to any disclaimer, the term of this patent is extended or adjusted under 35 U.S.C. 154(b) by 0 days.

(21) Appl. No.: 13/490,214

(22) Filed: Jun. 6, 2012

(51) Int. Cl.
*H01J 37/07* (2006.01)
*H01J 37/244* (2006.01)
*H01J 49/04* (2006.01)
*H01J 49/00* (2006.01)

(52) U.S. Cl.
CPC ............. *H01J 49/0004* (2013.01); *H01J 37/07* (2013.01); *H01J 37/244* (2013.01)

(58) Field of Classification Search
CPC ............ G21K 7/00; H01J 49/44; G01N 23/00
USPC ........................................................ 250/305
See application file for complete search history.

(56) References Cited

U.S. PATENT DOCUMENTS

| | | | |
|---|---|---|---|
| 5,772,760 A * | 6/1998 | Gruen et al. ............... | 117/104 |
| 6,103,305 A * | 8/2000 | Friedmann et al. ........ | 427/249.7 |
| 6,537,668 B1 * | 3/2003 | Vijayen et al. ............. | 428/408 |
| 6,586,735 B1 * | 7/2003 | Haking et al. .............. | 250/307 |
| 7,582,868 B2 * | 9/2009 | Jiang et al. ................. | 250/307 |
| 7,808,652 B2 | 10/2010 | Munteanu et al. | |
| 2004/0135081 A1 * | 7/2004 | Larson et al. .............. | 250/305 |
| 2007/0272664 A1 * | 11/2007 | Schroder et al. .......... | 219/121.59 |
| 2008/0199733 A1 * | 8/2008 | Oka ............................. | 428/810 |
| 2008/0210863 A1 * | 9/2008 | Pinna et al. ................ | 250/305 |
| 2010/0032571 A1 * | 2/2010 | Shelley et al. ............. | 250/341.8 |
| 2010/0044230 A1 * | 2/2010 | Papadimitrakopoulos et al. ........................ | 204/547 |
| 2010/0098970 A1 * | 4/2010 | Galbiati ..................... | 428/670 |
| 2010/0255984 A1 * | 10/2010 | Sutter et al. ............... | 502/185 |
| 2011/0063376 A1 * | 3/2011 | Morozumi et al. ........ | 347/68 |

OTHER PUBLICATIONS

Pulsed laser deposition of diamond-like carbon films David L. Pappas, Katherine L. Saenger, John Bruley, William Krakow, and Jerome J. Cuomo IBM Research, T. J. Watson Research Center, P.O. Box 218, Yorktown Heights, New York.*

Pappas, et al., "Pulsed laser deposition of diamond-like carbon films", J. Appl. Phys. 71 (11), Jun. 1, 1992, 10 pages.

* cited by examiner

*Primary Examiner* — Nicole Ippolito
*Assistant Examiner* — Sean Luck

(57) ABSTRACT

A method for characterizing a carbon overcoat is provided. The method includes performing electron energy loss spectroscopy (EELS) spectrum imaging for an area of a preselected carbon-based material and an area of the carbon overcoat to generate a reference EELS dataset and a carbon overcoat EELS dataset, respectively, and determining a carbon bonding content of the carbon overcoat based on the reference EELS dataset and the carbon overcoat EELS dataset.

14 Claims, 3 Drawing Sheets

METHODS FOR CHARACTERIZING CARBON OVERCOAT

FIELD

Aspects of the present invention relate to characterization of carbon overcoat, and, in particular, to processes and methods for characterizing ultra thin carbon overcoat.

BACKGROUND

With the continued scaling down of the magnetic head used in hard drives, improved magnetic signal-to-noise ratio in the magnetic head and media is needed for a new generation of hard drives. To improve performance, ultra thin (e.g., less than about 3 nm) carbon overcoat (COC) has been used in the fabrication of new generations of head and media. The carbon overcoat is fabricated to achieve the desired chemical state in order to ensure the mechanical and/or thermal properties needed for the prescribed performance specifications of the head and media. This can be partially achieved by using unpatterned full (or thick) film monitor coupons, that are used to monitor a workpiece wafer. The coupon is a separate wafer such as a silicon wafer that is processed in substantially the same way as the workpiece wafer.

However, the generally known characterization methods of thick films becomes unreliable when the thickness of the carbon overcoat is less than about 3 nm. It is because thin carbon overcoat is intrinsically and chemically different from thick films. Therefore, conventional characterization methods applied to thick films become unreliable and less sensitive in measuring thickness, composition, and chemical bonding when the film thickness drops below about 3 nm. Additionally, the carbon overcoat at different locations of a head has different properties depending on the areas, such as substrate, shield, where the carbon overcoat is grown on. Therefore, a reliable technique is needed to fully characterize the carbon overcoat used in head and media development and manufacturing processes.

Various methods have been used to characterize the chemical bonding information ($sp^3/sp^2$ ratio) of carbon overcoat films, such as Raman spectroscopy, solid-state nuclear magnetic resonance (NMR), X-ray photoelectron spectroscopy (XPS), and electron energy loss spectroscopy (EELS) in transmission electron microscopy (TEM). While Raman, NMR, and XPS are useful techniques, the carbon overcoat generally needs to have a thickness more than about 3 nm to carry out the measurement with a reasonable signal-to-noise ratio. While EELS can work on thinner films down to sub-nanometer in thickness, there is no known direct way to detect a $sp^3/sp^2$ ratio of a carbon overcoat (COC) using EELS.

SUMMARY

Embodiments of the present invention are directed to methods for fully characterizing an ultra thin (e.g., less than about 3 nm) carbon overcoat. Full characterization of the carbon overcoat includes determining the thickness of the carbon overcoat, which generally includes a carbon layer and a seed layer, the composition profile and two-dimensional map of the carbon overcoat, and the carbon chemical bonding $sp^3/sp^2$ ratio of the carbon overcoat.

A method for characterizing a carbon overcoat is provided according to one embodiment of the present invention. The method include: performing electron energy loss spectroscopy (EELS) spectrum imaging for an area of a preselected carbon-based reference material and an area of the carbon overcoat to generate a reference EELS dataset and a carbon overcoat EELS dataset, respectively; and determining a carbon bonding content of the carbon overcoat based on the reference EELS dataset and the carbon overcoat EELS dataset.

A method for characterizing a carbon overcoat is provided according to another embodiment of the present invention. The method includes: measuring a thickness of the carbon overcoat using transmission electron microscopy (TEM); measuring a thickness of a sub-layer of the carbon overcoat using energy filtered transmission electron microscopy (EFTEM) or scanning transmission electron microscopy (STEM), the sub-layer comprising carbon and a seed material; performing electron energy loss spectroscopy (EELS) spectrum imaging for an area of a preselected carbon-based material and an area of the carbon overcoat to generate a reference EELS dataset and a carbon overcoat EELS dataset; and determining a carbon bonding of the carbon overcoat based on the reference EELS dataset and the carbon overcoat EELS dataset, the carbon bonding selected from the group consisting of a $sp^3$ bonding and a $sp^2$ bonding.

BRIEF DESCRIPTION OF THE DRAWINGS

The above and other features and aspects of the present invention will become more apparent by describing in detail embodiments thereof with reference to the attached drawings in which.

DETAILED DESCRIPTION

Carbon can form a great variety of crystalline and disordered structures because carbon can exist in three hybridization states such as $sp^3$, $sp^2$, and $sp^1$. There is no known direct way to detect a $sp^3/sp^2$ ratio of a carbon overcoat (COC). However, a theoretical model has been known that can be used to calculate the $sp^3/sp^2$ ratio of a carbon overcoat from electron energy loss spectroscopy (EELS) of the carbon overcoat. However, the theoretical model has the following limitations: 1) it can produce satisfactory results for unpatterned full film having a film thickness of more than about 3 nm in order to carry out the EELS measurement with a good signal-to-noise ratio; 2) there are no known procedures to do the EELS measurement with good repeatability for patterned devices having a film thickness of less than about 3 nm; and 3) there is no known way to process the EELS data with good reliability and consistency. Embodiments of the present invention solve the above-described problems by utilizing EELS in an innovative way to provide a practical way of utilizing the theoretical model in real life applications.

Currently there is no reliable method to characterize the chemical state of an ultra thin (e.g., less than about 3 nm) carbon overcoat (e.g., diamond-like carbon) of nanometers localized at patterned device level. Embodiments of the present invention provide a characterization method for quantitatively characterizing and comparing relative $sp^3/sp^2$ ratio of a carbon overcoat directly on the nanometer sized device with sub-nanometer spatial resolution together with other information such as thickness and composition. This characterization method employs a combination of transmission electron microscopy (TEM), scanning transmission electron microscopy (STEM), energy filtered transmission electron microscopy (EFTEM), and/or electron energy loss spectroscopy (EELS).

High energy resolution (e.g., about 1 eV) EELS can be used to evaluate the $sp^3/sp^2$ ratio of carbon overcoats for head and media. The evaluation of the $sp^3/sp^2$ ratio can be accomplished by determining the relative intensity of pi bond ($\pi^*$) and sigma bond ($\sigma^*$) at the carbon K-edge of the EELS spectra of the carbon overcoat, and comparing the relative intensity to that of a preselected carbon-based reference material (hereafter "reference material") such as a material constituted of 100 percent $sp^2$ microcrystalline graphite reference or $C_{60}$. In various embodiments of the present invention, a number of procedures/processes are performed to characterize a carbon overcoat such as a patterned ultra thin (e.g., between about 1 nm to about 3 nm, inclusive). The characterization includes determining the thickness, composition, chemical bonds, and $sp^3/sp^2$ ratio of the carbon overcoat based on the theoretical model to be described below in more detail.

Application of Theoretical Model

Figure 1:
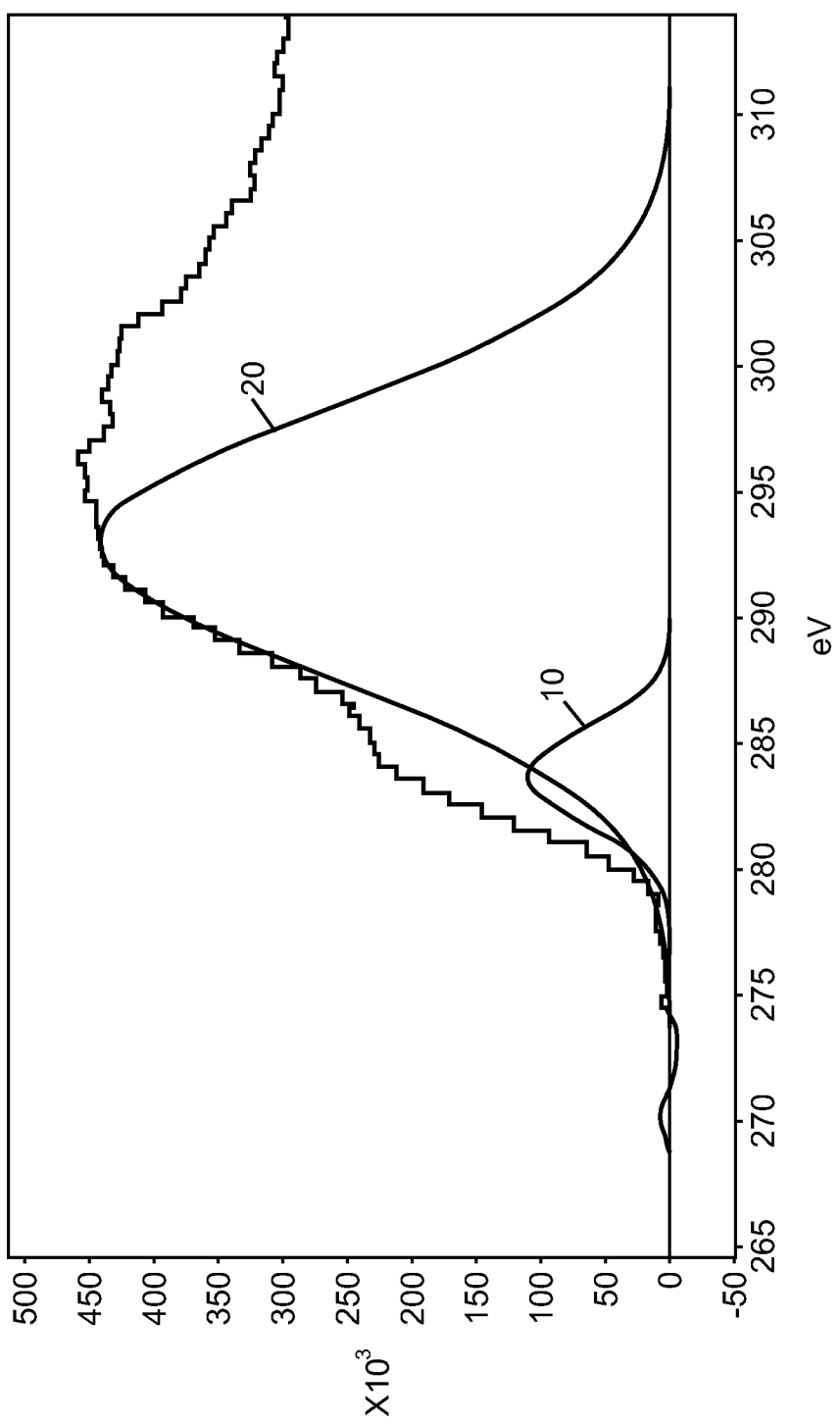
FIG. 1 is a graph illustrating electron energy loss spectroscopy spectrum for a carbon overcoat, the graph being fitted with curves for determining the pi orbital and sigma orbital peak intensities according to an embodiment of the present invention.

FIG. 1 is a graph illustrating electron energy loss spectroscopy spectrum for a carbon overcoat, the graph being fitted with curves (e.g., Gaussian curves) for determining the pi orbital and sigma orbital peak intensities according to an embodiment of the present invention. In FIG. 1, preselected energy windows are defined to fit a pi carbon bonding ($\pi^*$) curve 10 and a sigma carbon bonding ($\sigma^*$) curve 20, respectively, in order to determine the pi orbital intensity $I_\pi$ and sigma orbital intensity $I_\sigma$ through integration under the respective curves. The same processes are also performed on a reference material (e.g., 100 percent $sp^2$ carbon-based material). To a good approximation, the ratio of the integrated areas under the energy windows (e.g., 284 eV to 289 eV for $I_\pi$ and 290 eV to 305 eV for $I_\sigma$) is proportional to $N_\pi/N_\sigma$, which is a ratio of the number of $\pi$ and $\sigma$ orbitals. The ratio $N_\pi/N_\sigma$ is 1/3 for 100 percent $sp^2$ bonded carbon and 0/4 for 100 percent $sp^3$ bonded carbon. Therefore, the number of $sp^3$ bonded carbon atoms can be expressed as $N(sp^3)=(N_\sigma-3N_\pi)/4$, and the number of $sp^2$ bonded carbon atoms can be expressed as $N(sp^2)=N_\pi$. Accordingly, using a reference that contains 100 percent $sp^2$ bonded carbon atoms, the number fraction $F(sp^3)$ of $sp^3$ bonded atoms and the number fraction $F(sp^2)$ of $sp^2$ bonded atoms of the carbon overcoat (COC) can be determined by Equations (1) and (2).

$$F(sp^3) = \frac{1 - 3 \cdot \frac{N_\pi}{N_\sigma}}{1 + \frac{N_\pi}{N_\sigma}}, \text{ where} \qquad \text{Equation (1)}$$

$$\frac{N_\pi}{N_\sigma} = \frac{[I_\pi/I_\sigma]_{coc}}{3 \cdot [I_\pi/I_\sigma]_{reference}}$$

$$F(sp^2) = 1 - F(sp^3) \qquad \text{Equation (2)}$$

Here, $N_\pi$ is a number of carbon atoms having the $sp^2$ bonding, and $N_\sigma$ is a number of carbon atoms having the $sp^3$ bonding. $I_\pi$ is a pi orbital intensity, and $I_\sigma$ is a sigma orbital intensity, at a carbon K-edge. Therefore, using a reference material of 100 percent $sp^2$ bonded carbon atoms, the $sp^3/sp^2$ ratio of the carbon overcoat can be determined based on Equations (1) and (2).

In several embodiments, the carbon overcoat can include other elements (e.g., N, H, or O) in addition to carbon, and the carbon overcoat will have bondings between carbon and the other elements. Therefore, additional Gaussian curves can be fitted to account for the non-carbon-to-carbon bondings, and the corresponding $I_\pi$ and $I_\sigma$ of the non-carbon-carbon bondings can be subtracted. In such case, Equations (1) and (2) can still be used to determine the desired $sp^3/sp^2$ ratio of carbon-to-carbon bonding of the carbon overcoat.

Characterization Processes

Figure 2:
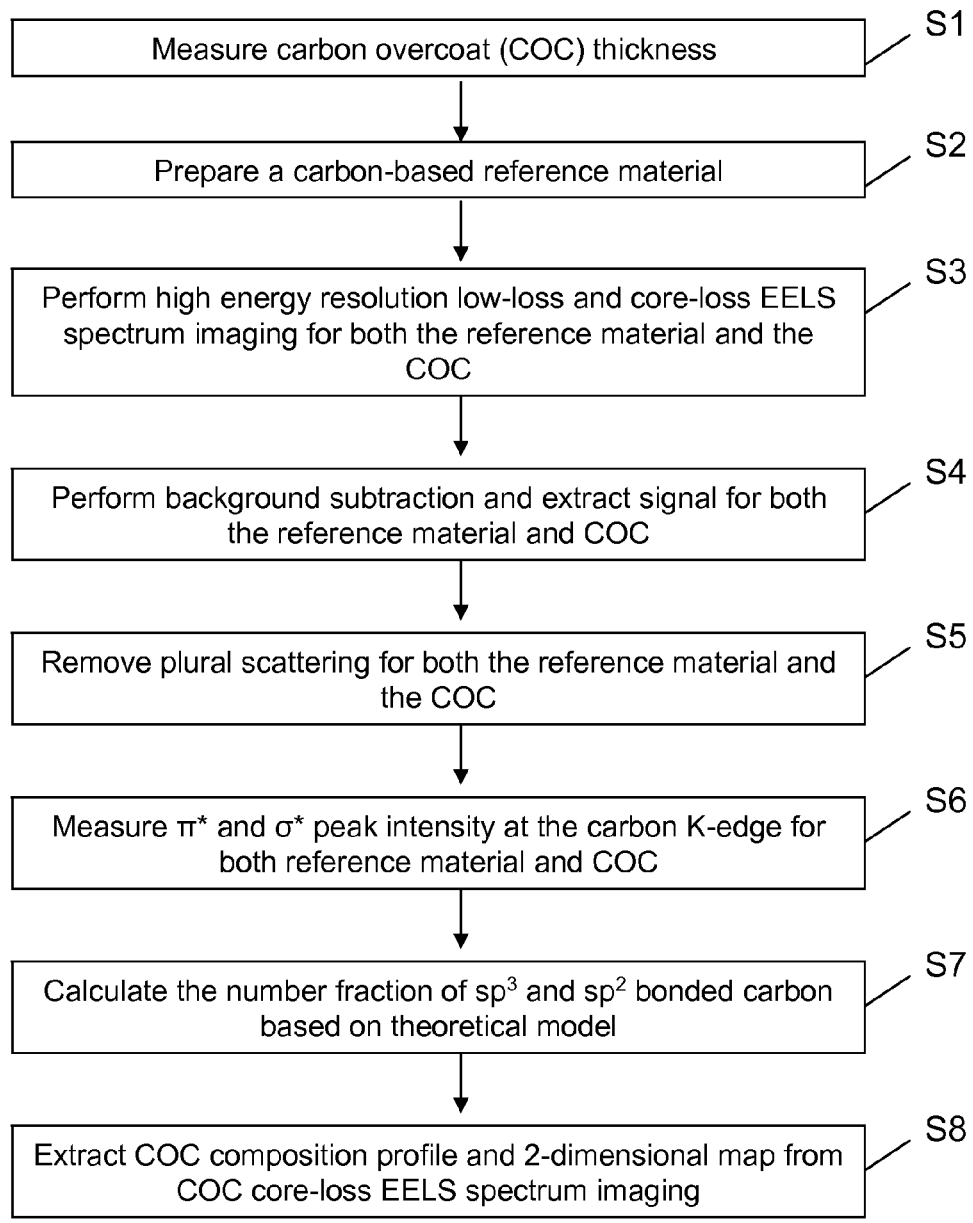
FIG. 2 is a flowchart illustrating a number of processes for fully characterizing a carbon overcoat according to an embodiment of the present invention.

FIG. 2 is a flowchart illustrating a number of processes for fully characterizing a carbon overcoat (e.g., a diamond-like carbon coating) according to an embodiment of the present invention. However, the present invention is not limited thereto. In various embodiments, the processes can be performed in different orders. In several embodiments, some of the processes can be omitted. In other embodiments, additional processes can be performed. In several embodiments, the processes can be applied to characterize a carbon overcoat of a magnetic head at wafer, slider, and head gimbal assembly (HGA) level. In one embodiment, the processes can be used to characterize the carbon overcoat of magnetic media.

To fully characterize a carbon overcoat, the processes determine the thickness of the carbon overcoat including the thickness of a carbon layer and a seed layer of the carbon overcoat, the composition profile and two-dimensional map of the carbon overcoat, and the carbon chemical bonding $sp^3/sp^2$ ratio of the carbon overcoat. The processes will be described in more detail in reference to FIG. 2 as a non-limiting example. Referring to block S1 of FIG. 2, a thickness of a carbon overcoat is measured using a microscopy technique such as transmission electron microscopy (TEM) and scanning transmission electron microscopy (STEM). Further, a thickness of carbon and a seed material (a sub-layer) of the carbon overcoat is measured using a microscopy technique such as energy filtered transmission electron microscopy (EFTEM) and STEM.

Referring to block S2 of FIG. 2, a preselected carbon-based material (hereafter "reference material") is used as a reference for characterizing the carbon overcoat using electron energy loss spectroscopy (EELS). In several embodiments, the reference material includes substantially 100 percent $sp^2$ bonded carbon (e.g., microcrystalline graphite) such that EELS orientation dependence effect can be eliminated. For example, when the reference material is a microcrystalline graphite, the electron density of such material is substantially the same in any of the possible orientations. In one embodiment, the reference material includes $C_{60}$.

Referring to block S3 of FIG. 2, EELS spectrum imaging is performed on a preselected area of the reference material and a preselected area of the carbon overcoat to generate a reference EELS spectrum imaging dataset and a carbon overcoat EELS spectrum imaging dataset, respectively. In more detail, the EELS spectrum imaging includes performing a high energy resolution (e.g., about 1 eV) low-loss EELS spectrum imaging and core-loss EELS spectrum imaging for both the area of the reference material and the area of the carbon overcoat.

In block S4 of FIG. 2, background subtraction is performed on the reference EELS dataset and the carbon overcoat EELS dataset to remove the background from the EELS datasets to extract signals for both the reference material and the carbon overcoat. The background of an EELS spectrum can originate from multiple inelastic electron scatterings and extension of previous absorption edges. In one embodiment, background subtraction is performed by fitting a power-law function to the observed background. However, the present invention is not limited thereto. In several embodiments, other suitable background subtraction methods such as a differentiation method can be used.

In block S5 of FIG. 2, Fourier-ratio deconvolution is performed to remove plural scattering, which can be generated by electrons that undergo multiple inelastic scattering events primarily due to the larger physical thickness than the mean free path of the inelastic scattering, for both the reference material and the carbon overcoat so that the reference EELS dataset and the carbon overcoat EELS dataset can be further processed irrespective of the difference in thickness between the reference material and the carbon overcoat. However, the present invention is not limited to using Fourier-ratio deconvolution. In several embodiments, other suitable methods such as Fourier-log deconvolution can be used to account for the thicknesses of the reference material and the carbon overcoat.

In block S6 of FIG. 2, the $\pi^*$ and $\sigma^*$ peak intensities ($I_\pi$ and $I_\sigma$) are determined or measured at the carbon K-edge for both the reference material and the carbon overcoat using, for example, a non-linear least squares (NLLS) fitting method according to an embodiment of the present invention. However, the present invention is not limited thereto. In several embodiments, other suitable fitting methods can be used. Referring back to FIG. 1, the EELS spectra are fitted with Gaussian curves by NLLS for determining the peak intensities ($I_\pi$ and $I_\sigma$) according to an embodiment of the present invention. The peak intensities ($I_\pi$ and $I_\sigma$) can be determined according to Equations (3) and (4).

$$I_\pi = (A)_\pi \times (FWHM)_\pi \quad (3)$$

$$I_\sigma = (A)_\sigma \times (FWHM)_\sigma \quad (4)$$

In Equations (3) and (4), A is the amplitude of the corresponding Gaussian curve, and FWHM is the full width at half maximum of the Gaussian curve. The processes of block S6 are performed on both the carbon overcoat EELS dataset and reference EELS dataset.

In block S7, the number fraction of $sp^3$ bonded atoms and the number fraction of $sp^2$ bonded atoms of the carbon overcoat can be determined using the above-described Equations (1) and (2) using the peak intensities ($I_\pi$ and $I_\sigma$) determined in block S6. The processes described in reference to blocks S2 through S7 provide a method for quantifying the $sp^3$ carbon and $sp^2$ carbon content of the carbon overcoat according to an embodiment of the present invention. Therefore, the $sp^3/sp^2$ ratio of the carbon overcoat can be determined.

In block S8, the composition profile and two-dimensional map of the carbon overcoat are extracted in the core-loss EELS spectrum from the carbon overcoat EELS dataset. In one embodiment, the information can be extracted using suitable software. In one embodiment, software sold under the trademark DigitalMicrograph®, which is made by Gatan, Inc. of Pleasanton in California, can be used to control the spectrometer, data acquisition, and data processing.

The above described processes can be used to fully characterize a carbon overcoat having a thickness of 3 nm or less. In several embodiments, the disclosed processes can be used to fully characterize a carbon overcoat of magnetic head or media. In other embodiments, the disclosed processes can be used to characterize a carbon overcoat at device level such as wafer, slider, and HGA. Therefore, the processes of the present invention can be used to evaluate and compare carbon overcoats quantitatively in ultra thin carbon overcoat development and manufacturing.

Figure 3:
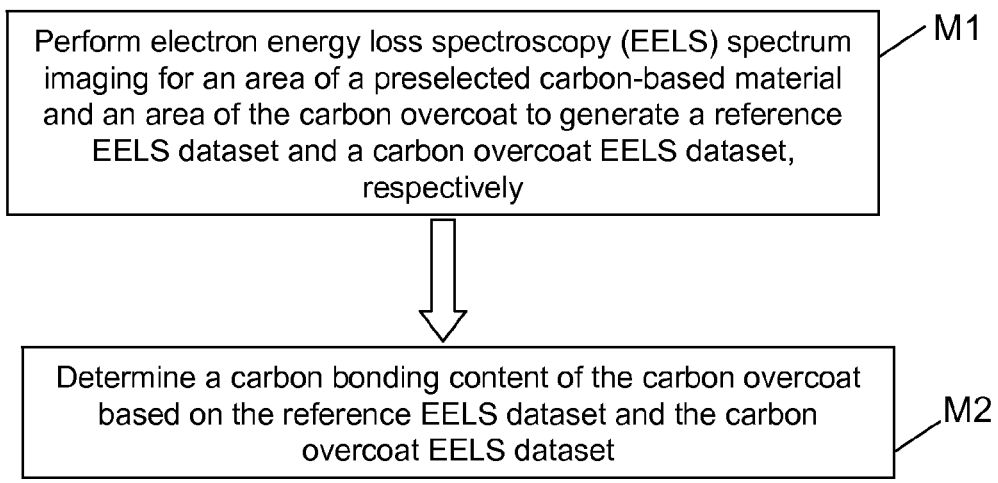
FIG. 3 is a flowchart illustrating a method for characterizing a carbon overcoat according to an embodiment of the present invention.

FIG. 3 is a flowchart illustrating a method for characterizing a carbon overcoat according to an embodiment of the present invention. In block M1 of FIG. 3, EELS spectrum imaging is performed for an area of a preselected carbon-based material and an area of a carbon overcoat to generate a reference EELS dataset and a carbon overcoat EELS dataset, respectively. In block M2 of FIG. 3, a carbon bonding content of the carbon overcoat is determined using the reference EELS dataset and the carbon overcoat EELS dataset. In several embodiments, some or all of the processes described in reference to FIG. 2 can be applied in block M2 to determine the carbon bonding content of the carbon overcoat.

In the above described embodiments, the process or method can perform the sequence of actions in a different order. In another embodiment, the process or method can skip one or more of the actions. In other embodiments, one or more of the actions are performed simultaneously or concurrently. In some embodiments, additional actions can be performed.

While the present invention has been particularly shown and described with reference to embodiments, it will be understood by those of ordinary skill in the art that various changes in form and details may be made therein without departing from the spirit and scope of the present invention as defined by the following claims and their equivalents.

What is claimed is:

1. A method for characterizing a carbon overcoat with a thickness of three nanometers or less, comprising:
   performing electron energy loss spectroscopy (EELS) spectrum imaging for an area of a preselected carbon-based material and an area of a carbon overcoat of a magnetic head or a magnetic data storage medium to generate a reference EELS dataset and a carbon overcoat EELS dataset, respectively,
   wherein the carbon overcoat has a thickness of three nanometers or less,
   wherein the performing EELS spectrum imaging comprises performing high energy resolution low-loss EELS spectrum imaging and core-loss EELS spectrum imaging for both the area of the preselected carbon-based material and the area of the carbon overcoat;
   removing plural scattering in both the reference EELS dataset and the carbon overcoat EELS dataset to account for the difference in thickness between the preselected carbon-based material and the carbon overcoat;
   quantifying a ratio of $sp^3$ bonding to $sp^2$ bonding of the carbon overcoat based on the reference EELS dataset and the carbon overcoat EELS dataset; and extracting a carbon overcoat element profile and a two-dimensional map of the carbon overcoat in the core-loss EELS spectrum from the carbon overcoat EELS dataset.

2. The method of claim 1, further comprising measuring a thickness of the carbon overcoat using a microscopy technique selected from the group consisting of transmission electron microscopy (TEM) and scanning transmission electron microscopy (STEM).

3. The method of claim 2, further comprising measuring a thickness of a sub-layer of the carbon overcoat, the sub-layer comprising carbon and a seed material.

4. The method of claim 3, wherein the thickness of the sub-layer of the carbon overcoat is measured using a microscopy technique selected from the group consisting of energy filtered transmission electron microscopy (EFTEM) and scanning transmission electron microscopy (STEM).

5. The method of claim 1, wherein the preselected carbon-based material comprises a material selected from the group consisting of microcrystalline graphite and $C_{60}$.

6. The method of claim 1, wherein the preselected carbon-based material comprises substantially 100 percent $sp^2$ carbon bonding.

7. The method of claim 1, further comprising performing power-law background subtraction on the reference EELS dataset and the carbon overcoat EELS dataset to extract signals for both the preselected carbon-based material and the carbon overcoat.

8. The method of claim 1, wherein the quantifying the ratio of $sp^3$ bonding to $sp^2$ bonding of the carbon overcoat comprises:

determining a pi orbital intensity ($I_\pi$) and a sigma orbital intensity ($I_\sigma$) at a carbon K-edge for both the carbon overcoat and the preselected carbon-based material using the EELS datasets; and calculating a number fraction of $sp^3$ bonding and a number fraction of $sp^2$ bonding of the carbon overcoat based on the following equations:

$$F(sp^3) = \frac{1 - 3 \cdot \frac{N_\pi}{N_\sigma}}{1 + \frac{N_\pi}{N_\sigma}}, \text{ where}$$

$$\frac{N_\pi}{N_\sigma} = \frac{[I_\pi / I_\sigma]_{coc}}{3 \cdot [I_\pi / I_\sigma]_{reference}}, \text{ and}$$

$$F(sp^2) = 1 - F(sp^3),$$

where $F(sp^3)$ is the number fraction of the $sp^3$ bonding, $F(sp^2)$ is the number fraction of the $sp^2$ bonding, $N_\pi$ is a number of carbon atoms having the $sp^2$ bonding, and $N_\sigma$ is a number of carbon atoms having the $sp^3$ bonding.

9. The method of claim 8, wherein the quantifying the ratio of $sp^3$ bonding to $sp^2$ bonding of the carbon overcoat further comprises removing plural scattering by Fourier-Ratio in both the reference EELS dataset and the carbon overcoat EELS dataset.

10. The method of claim 8; wherein the quantifying the ratio of $sp^3$ bonding to $sp^2$ bonding of the carbon overcoat further comprises applying a non-linear least squares (NLLS) fitting on both the reference EELS dataset and the carbon overcoat dataset to determine the $I_\pi$ and $I_\sigma$.

11. The method of claim 1, wherein the carbon overcoat comprises a diamond-like carbon.

12. A method for characterizing a carbon overcoat with a thickness of three nanometers or less, comprising:

measuring a thickness of a carbon overcoat of a magnetic head or a magnetic data storage medium using transmission electron microscopy (TEM), wherein the carbon overcoat has a thickness of three nanometers or less;

measuring a thickness of a sub-layer of the carbon overcoat using energy filtered transmission electron microscopy (EFTEM) or scanning transmission electron microscopy (STEM), the sub-layer comprising carbon and a seed material;

performing electron energy loss spectroscopy (EELS) spectrum imaging for an area of a preselected carbon-based material and an area of the carbon overcoat to generate a reference EELS dataset and a carbon overcoat EELS dataset, wherein the performing EELS spectrum imaging comprises performing high energy resolution low-loss EELS spectrum imaging and core-loss EELS spectrum imaging for both the area of the preselected carbon-based material and the area of the carbon overcoat;

removing plural scattering in both the reference EELS dataset and the carbon overcoat EELS dataset to account for the difference in thickness between the reference preselected carbon-based material and the carbon overcoat;

quantifying a ratio of $sp^3$ bonding to $sp^2$ bonding of the carbon overcoat based on the reference EELS dataset and the carbon overcoat EELS dataset; and extracting a carbon overcoat element profile and a two-dimensional map of the carbon overcoat in the core-loss EELS spectrum from the carbon overcoat EELS dataset.

13. The method of claim 12, wherein the TEM is scanning transmission electron microscopy (STEM).

14. The method of claim 12, wherein the quantifying a ratio of $sp^3$ bonding to $sp^2$ bonding of the carbon overcoat comprises:

determining a pi orbital intensity ($I_\pi$) and a sigma orbital intensity ($I_\sigma$) at a carbon K-edge for both the carbon overcoat and the preselected carbon-based material using the EELS datasets; and calculating a number fraction of the $sp^3$ bonding and a number fraction of the $sp^2$ bonding of the carbon overcoat based on the following equations:

$$F(sp^3) = \frac{1 - 3 \cdot \frac{N_\pi}{N_\sigma}}{1 + \frac{N_\pi}{N_\sigma}}, \text{ where}$$

$$\frac{N_\pi}{N_\sigma} = \frac{[I_\pi / I_\sigma]_{coc}}{3 \cdot [I_\pi / I_\sigma]_{reference}}, \text{ and}$$

$$F(sp^2) = 1 - F(sp^3),$$

where $F(sp^3)$ is the number fraction of the $sp^3$ bonding, $F(sp^2)$ is the number fraction of the $sp^2$ bonding $N_\pi$ is a number of carbon atoms having the $sp^2$ bonding, and $N_\sigma$ is a number of carbon atoms having the $sp^3$ bonding.

* * * * *